United States Patent
Schmid et al.

(10) Patent No.: US 6,761,681 B2
(45) Date of Patent: Jul. 13, 2004

(54) PERCUTANEOUS OR TRANSCUTANEOUS ACCESS INTO THE BODY

(75) Inventors: Christoph Hans Schmid, Zollikofen (CH); Herbert Baechler, Meilen (CH)

(73) Assignee: Phonak AG, Stafa (CH)

( * ) Notice: Subject to any disclaimer, the term of this patent is extended or adjusted under 35 U.S.C. 154(b) by 0 days.

(21) Appl. No.: 09/929,203

(22) Filed: Aug. 14, 2001

(65) Prior Publication Data

US 2003/0034039 A1 Feb. 20, 2003

(51) Int. Cl.⁷ .............................. A61N 2/00; H04R 25/00
(52) U.S. Cl. ................ 600/9; 600/15; 600/25
(58) Field of Search ................ 600/9, 15, 25, 600/30; 128/876, 899; 623/11.11; 607/57

(56) References Cited

U.S. PATENT DOCUMENTS

| | | | |
|---|---|---|---|
| 3,952,726 A | * | 4/1976 | Hennig et al. ............... 600/30 |
| 4,004,298 A | | 1/1977 | Freed |
| 4,025,964 A | * | 5/1977 | Owens ..................... 623/11.11 |
| 4,258,705 A | * | 3/1981 | Sorensen et al. .............. 600/30 |
| 4,352,960 A | | 10/1982 | Dormer et al. |
| 4,628,907 A | * | 12/1986 | Epley .......................... 600/25 |
| 4,726,378 A | | 2/1988 | Kaplan |
| 4,994,019 A | * | 2/1991 | Fernandez et al. ............ 600/30 |
| 5,017,185 A | * | 5/1991 | Baermann ..................... 600/15 |
| 5,144,952 A | | 9/1992 | Frachet et al. |
| 5,450,858 A | * | 9/1995 | Zablotsky et al. .......... 128/876 |
| 5,507,303 A | | 4/1996 | Kuzmam |
| 5,545,191 A | * | 8/1996 | Mann et al. .................. 607/57 |
| 5,782,743 A | * | 7/1998 | Russell .......................... 600/9 |
| 5,949,895 A | | 9/1999 | Ball et al. |

FOREIGN PATENT DOCUMENTS

WO     WO 9222107 A1 * 12/1992 ........... A61F/11/04

\* cited by examiner

*Primary Examiner*—Mary Beth Jones
*Assistant Examiner*—Nikita R Veniaminov
(74) *Attorney, Agent, or Firm*—Pearne & Gordon LLP

(57) ABSTRACT

A percutaneous or transcutaneous connecting device, featuring at least one passage or a passage-free connection through the outer surface and in particular the skin of a living being, incorporates a permanent magnet (7) which is positioned in the area of the outer surface such as the skin (1, 3) with its poles essentially extending parallel thereto. In the case of a percutaneous connecting device, physical passages (9) are provided which extend through the outer surface of the living being, whereas in the case of a transcutaneous connecting device the transfer of electrical or electromagnetic signals and/or electrical energy takes place without physical passages, instead employing for instance coils.

13 Claims, 2 Drawing Sheets

US 6,761,681 B2

PERCUTANEOUS OR TRANSCUTANEOUS ACCESS INTO THE BODY

BACKGROUND OF THE INVENTION

This invention relates to a percutaneous or transcutaneous connecting device as conceptually specified in claim 1, to possible uses of the device, and to a method as conceptually specified in claim 12.

In technical literature and patents one finds a wide variety of devices for access into the human body. Artificial access ports of that nature are needed for applications such as the administration of medication or the introduction of electrical signals or electrical energy into the body.

There is a basic difference between percutaneous and transcutaneous access ports. Percutaneous access ports extend in physical, mechanical fashion through the skin. Transcutaneous access does not usually involve access hardware but often employs the induction principle, creating an electrical connection between the inside of the body and its external surroundings.

Apart from their functional connection, such access ports are designed with particular consideration given to their assimilative compatibility at the point of implantation and to the need for minimizing the risk of infection. In addition, it must be possible for the patients, or for their medical care providers in any event, to make or break the connection as quickly as possible (user friendliness).

Both WO98/51367 and WO99/34754 propose purely mechanical plug-type junctions for connecting and disconnecting the access port. For attaching electrical lead wires as well as for administering fluids the junction must necessarily permit exposure to a certain minimum coupling pressure, thus requiring relatively complex designs and making the connect and disconnect operation awkward for the user. To avoid that, U.S. Pat. No. 5,507,303 proposes, inter alia, to generate the necessary coupling pressure by magnetostatic means. To that effect, both the implanted part and the external plug-in element each contain a magnet that assures adequate coupling pressure. Guiding and aligning the external part relative to the implanted part of the access port is still done in mechanical fashion.

U.S. Pat. No. 5,949,895 describes a transcutaneous connection consisting of a pair of flat, symmetrical coils which are aligned with a pair of symmetric, cylindrical permanent magnets. This latter design on its part is relatively complex and not user-friendly.

BRIEF SUMMARY OF THE INVENTION

It is therefore an objective of this invention to provide a percutaneous or transcutaneous connection with the body of a living being and especially of a human which avoids the above-mentioned drawbacks.

The objective of this invention is achieved by means of a connecting device as specified in claim 1.

The devices per this invention for percutaneous or transcutaneous access into the body utilize magnetostatic forces both for providing the necessay coupling pressure and for aligning and positioning the external part of the access port relative to the implanted part. The result is a junction which the user can handle with significantly greater ease. Positioning can be facilitated by using asymmetric, for instance elongated permanent magnets. The north and south poles of the magnets do not line up toward the inside of the body as described in U.S. Pat. No. 5,507,303 but, instead, along the body opening. In other words, the permanent magnet and its poles extend parallel to the surface skin of the body.

Of particular advantage is a connection between the inside of the body and the external area of the body which is inherently asymmetric. This is true for instance when multiple individual passages in the case of a percutaneous connection cannot be configured symmetrically. It is also a factor when two asymmetric, flat coils of a transcutaneous connection must be aligned with each other.

BRIEF DESCRIPTION OF THE DRAWINGS

The following describes in more detail an implementation example of this invention with reference to the attached drawings in which—

DETAILED DESCRIPTION OF THE INVENTION

Figure 1A:
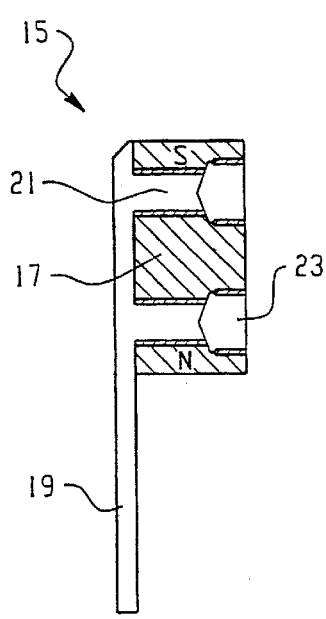
FIG. 1 is a longitudinal section view of a percutaneous connection with two separate passages.
Figure 1B:
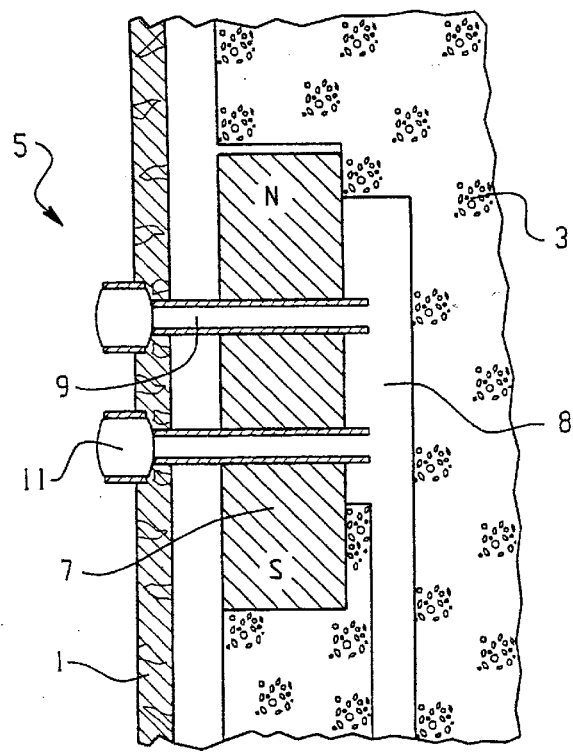

FIG. 1 is a lengthwise sectional view of a percutaneous two-part connection with two separate passages. One internal part 5 incorporates a permanent magnet 7 positioned beneath the epidermis 1 in the area of the corium or on a bone 3 underneath the epidermis. The north and south poles of the permanent magnet 7 are identified by N and S, respectively. Extending through the permanent magnet are two passages 9 each of which has a flared opening 11 that protrudes slightly from the epidermis 1. This, of course, is an example only and the device may instead be provided with only one or with multiple passages, and the passages do not necessarily have to feature a flared opening 11.

On the inside, the passages open into an area, marked 8, that serves for the connection of intake and/or exit conduits.

The counterpart to that is an external plug-in part 15 which on its part incorporates a permanent magnet 17 with a south and a north pole, respectively marked S and N. Extending from an intake/exit conduit 19, consisting for example of flexible tubing, and through the permanent magnet 17 are two ports 21 which on their part have each one connecting opening 23 facing the openings 11 and which may for instance be so dimensioned that the external part 15 can be plugged into the two openings 11. If the two permanent magnets are not powerful enough to hold the external part 15 in place on the permanent magnet 7, additional retaining features such as click-stop detents may be provided.

The conduits in the internal part 5 and in the external plug-in part 15 are so designed as to permit the introduction of substances such as medication, nutrients and the like, as well as the withdrawal of fluids from inside the body, an example of the latter being haemodialysis.

Figure 2A:
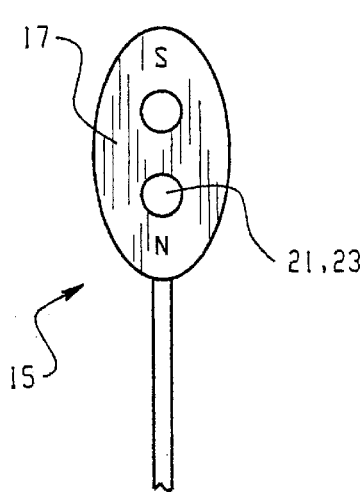
FIG. 2 is a top view of the magnets illustrated in FIG. 1.
Figure 2B:
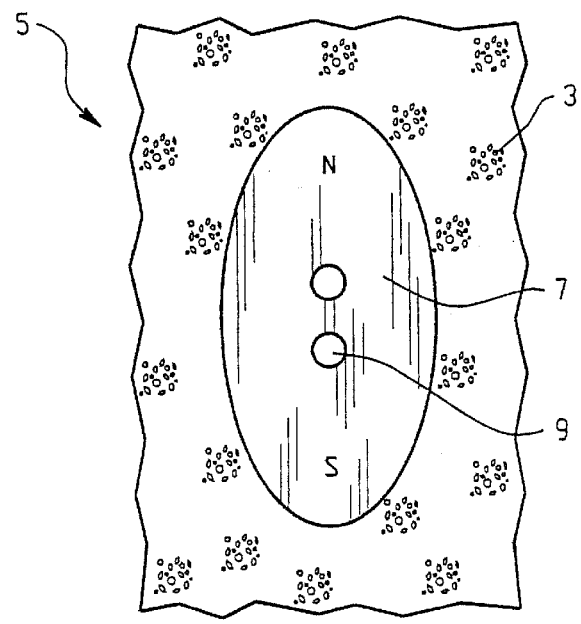

FIG. 2 includes an outside top view of the permanent magnet 7, visible by omitting an illustration of the epidermis 1 and of the corium or of the bone 3 underneath the epidermis. Clearly depicted are the two passages 9 extending vertically through the permanent magnet 7. Of course, the permanent magnet which in FIG. 2 has an oblong, oval shape may be configured differently, for instance rectangular, rod-shaped etc.

Analogous thereto, fig. 2 also includes a top view of the external plug-in part 15 consisting primarily of the permanent magnet 17 and the access ports 21 designed for plug-in connection with the passages 9. Of course, the external magnet 17 does not have to be in the form of an oblong oval but may be configured differently in adaptation to the shape of the permanent magnet 7. Indeed, it is even possible to install in the external part 15 a coil that generates a magnetic field, since the external magnet 17 does not necessarily have to be a permanent magnet.

Figure 3:
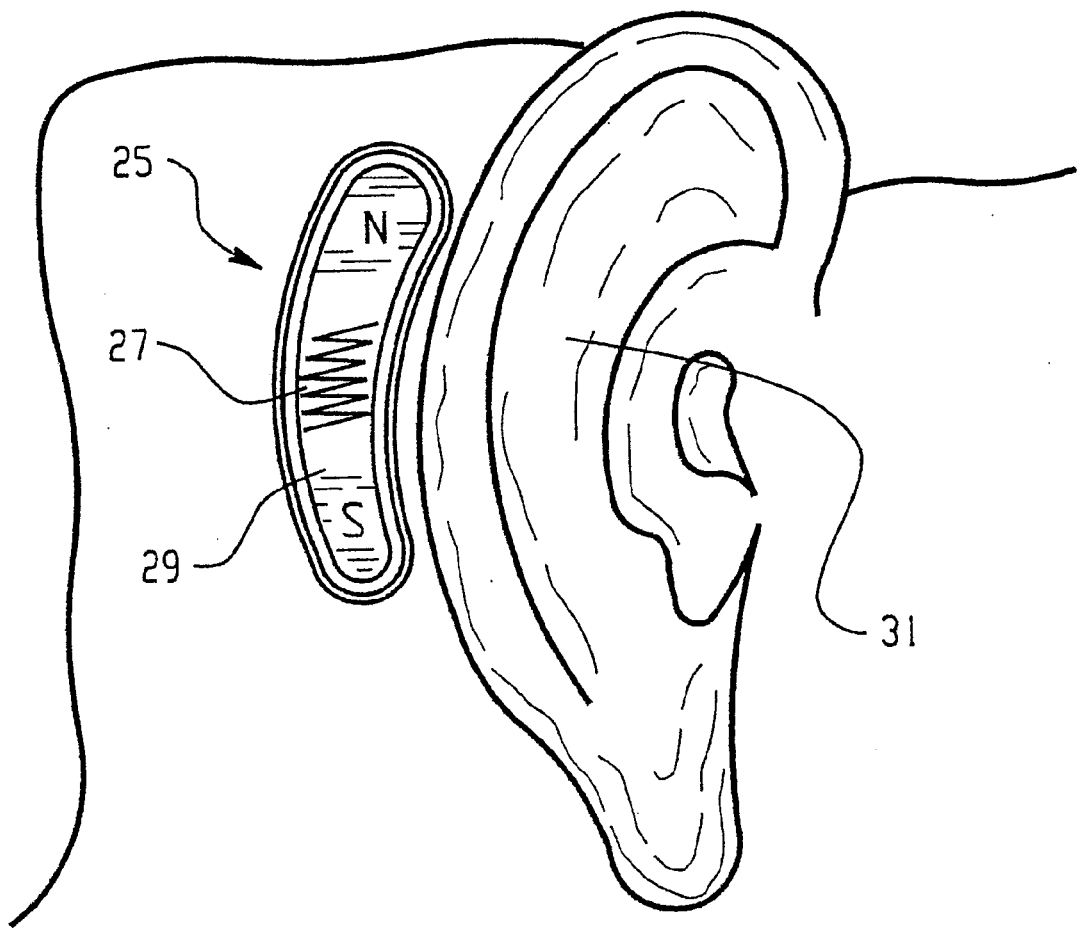
FIG. 3 schematically depicts a transcutaneous connection with two flat, physiologically shaped coils in the area of the outer ear.

Finally, FIG. 3 illustrates a possible application of the device per this invention in the form of a transcutaneous connection with two flat, physiologically adapted coils in the area of a human ear 31.

Given the anatomical and physiological conditions in that area, circular coils as frequently used in transcutaneous connections are not suitable. Instead, in this case a pair of oval, kidney-shaped or otherwise asymmetrically shaped coils must be given preference.

The implanted part 25 of a transcutaneous connection contains a coil 27 which serves to receive or, as the case may be, send electrical signals or to transfer electrical energy. The implanted part 25 also incorporates a permanent magnet 29 which serves to align and to retain in place an external part in relation to the implanted part. Such retention may be necessary especially when the coils are not carrying electric currents. Both the coil 27 and the permanent magnet 29 are implanted underneath the skin and are not visible from the outside. Therefore, in contrast to percutaneous connections, there is no physical, mechanical passage from inside the body to the outside or from the outside to the inside of the patient. This system is depicted in FIG. 3, with any illustration of the epidermis above the implanted part omitted so as to make the implant visible.

The external part (not shown) of the transcutaneous connection is similarly equipped with a coil for transferring signals or electric energy and with a permanent magnet for positioning and retention purposes. The area of the external part of the connection facing the implanted part is made of materials and provided with a surface which are compatible with the skin and permit wearing comfort. In terms of their geometric shape and their magnetic strength, the pair of permanent magnets are so dimensioned as to cause the external part of the connection to optimally align and position itself above the implanted part the moment it is brought near the implant. Optimal alignment is established when the inductive coupling between the coils in their particular geometric shape, dictated by the wearer's anatomy, is at a maximum level. The positioning and retentive function of the permanent magnets works in this transcutaneous system as well since the effect of the magnetostatic field extends through the skin.

Of course, the connections illustrated in FIGS. 1–3 merely constitute possible examples and this invention is not limited to the implementation examples shown. It follows that the widest range of variations is conceivable in terms of the design of the permanent magnets, the location of the permanent magnet directly in the epidermis or beneath the epidermis or in the bone, etc., or of the use of one, two or multiple passages, or of inductive, capacitive or other passage-free connections etc., or the configuration of the external plug-in part, or other features.

What is claimed is:

1. A percutaneous or connecting device with for providing a connection through an outer surface of a living being, characterized by a permanent magnet (7, 29) adapted to be positioned in the area of the outer surface (1, 3) with its poles extending essentially parallel thereto, wherein the permanent magnet (7) is adapted to be positioned through or underneath the epidermis and at least one passage (9) is proved in said magnet, wherein the device includes a functional element (15) connectable to the passage and containing an additional magnet (17), wherein the permanent magnet (7) and the additional magnet (17) are provided with positioning elements (11, 23) which serve to link at least one conduit (19) of the functional element with the passage (9).

2. The connecting device as in claim 1, wherein an opening (11) of the passage (9) and corresponding connecting opening (23) of the conduit (19) also serve as the positioning elements for connecting the functional element (15) in positionally correct fashion to the permanent magnet (7) and hold it there in a manner that it is comfortable for a wearer.

3. The connecting device as in claim 1, wherein the permanent magnet (29) and the additional magnet (17) are oblong in shape.

4. The connecting device as in claim 1, wherein the at least one passage (9) is connected to at least one conduit of the functional element, and said passage and conduit which in relation to a plane perpendicular to the magnets (7,17) extend in asymmetrical fashion.

5. The device as in any of the claims 1–2 or 3–4, wherein the device provides at least one connection extending from the functional element to the permanent magnet to administer medication or other substances, receive or transmit electrical signals or transfer electrical energy, place a measuring probe within the area of the skin of the living being, or collect samples or other substances from within the living being.

6. A percutaneous or transcutaneous connecting device for providing a connection through an outer surface of a living being characterized by a permanent magnet (7, 29) adapted to be positioned in the area of the outer surface (1,3) with its poles extending essentially parallel thereto, and at least one inductive, capacitive or other passage-free connection adapted to be between inside and outside of the body of a wearer.

7. The device as in claim 6, wherein the device provides a transcutaneous connection in the area of an outer ear (31) of a human, incorporating at least one coil (27) in the area of the permanent magnet (29) to receive or transmit electrical signals and/or transfer electrical energy.

8. A percutaneous or transcutaneous connecting device for providing a connection through an outer surface of a living being, characterized by a permanent magnet (7, 29) adapted to be positioned in the area of the outer surface (1,3) with its poles extending essentially parallel thereto, wherein in the area of the permanent magnet (29) at least one coil (27) is provided for the purpose of receiving or, respectively, sending electrical or electromagnetic signals and/or for transferring electrical energy.

9. A method for the transcutaneous or percutaneous introduction or withdrawal of medication, samples, or other substances into or from inside a living being, for transferring, receiving or transmitting electrical signals or electrical energy into or from inside a living being or for placing a measuring probe in the area of an outer surface of a living being, characterized in that, in the area of the outer surface of the living being, a permanent magnet is placed with its poles extending essentially parallel to that surface, wherein for the percutaneous or transcutaneous feed-through, transmission or placement, an external functional element is added on the outer surface of the living being which element as well contains an additional magnet and/or a coil, wherein a magnetic field retains the external functional element adhering to the permanent magnet in the area of the outer surface.

10. The method as in claim 9, wherein the medication, samples, or other substances are introduced into, or withdrawn from inside, the body of the living being via passages extending from the external functional element to the permanent magnet.

11. The method as in claim 9, wherein electrical or electromagnetic signals and/or electrical energy are conveyed by passage-free transmission from the external functional element to the permanent magnet, and vice versa, by means of at least one coil positioned in the area of the permanent magnet and, respectively, in the area of the external functional element.

12. A transcutaneous connecting device providing transcutaneous access through a skin surface comprising:

an external part and an internal part, the internal part adapted to be implanted beneath the skin surface;

a first magnetic member positioned within the internal part, said first magnetic member having north and south poles adapted to extend parallel to the skin surface; and a second magnetic member positioned within the external part, the second magnetic member having north and south poles adapted to extend parallel to the skin surface, wherein the second magnetic member aligns and magnetically retains in place the external part to the internal part when the second magnet member is positioned on the skin surface proximate to the first magnetic member; and at least one conduit extending through the external part.

13. A percutaneous connecting device providing percutaneous access through a skin surface comprising:

an external part and an internal part, the internal part adapted to be implanted beneath the skin surface;

a first magnetic member positioned within the internal part, the first magnetic member having north and south poles that extend parallel to the skin surface;

a second magnetic member positioned within the external part, the second magnetic member having north and south poles that extend parallel to the skin surface, wherein the second magnetic member aligns and magnetically retains in place the external part to the internal part when the second magnet member is positioned on the skin surface and proximate to the first magnetic member;

at least one passage extending through the internal part and opening on the skin surface; and at least one conduit extending through the external part; the conduit having a connecting opening that connects to the opening of the passage.

* * * * *

UNITED STATES PATENT AND TRADEMARK OFFICE
CERTIFICATE OF CORRECTION

PATENT NO. : 6,761,681 B2
DATED : July 13, 2004
INVENTOR(S) : Christoph Hans Schmid It is certified that error appears in the above-identified patent and that said Letters Patent is hereby corrected as shown below:

<u>Column 3,</u>
Line 63, please delete "device with for", and insert therefor -- device for --.

Signed and Sealed this

Twenty-fourth Day of August, 2004

JON W. DUDAS
*Director of the United States Patent and Trademark Office*

(12) INTER PARTES REVIEW CERTIFICATE (2944th)
United States Patent
Schmid et al.

(10) Number: US 6,761,681 K1
(45) Certificate Issued: Dec. 22, 2022

(54) PERCUTANEOUS OR TRANSCUTANEOUS ACCESS INTO THE BODY

(75) Inventors: Christoph Hans Schmid; Herbert Baechler

(73) Assignee: SONOVA AG

Trial Number:

IPR2020-00176 filed Nov. 26, 2019

Inter Partes Review Certificate for:

Patent No.: 6,761,681
Issued: Jul. 13, 2004
Appl. No.: 09/929,203
Filed: Aug. 14, 2001

The results of IPR2020-00176 are reflected in this inter partes review certificate under 35 U.S.C. 318(b).

INTER PARTES REVIEW CERTIFICATE
U.S. Patent 6,761,681 K1
Trial No. IPR2020-00176
Certificate Issued Dec. 22, 2022

AS A RESULT OF THE INTER PARTES REVIEW PROCEEDING, IT HAS BEEN DETERMINED THAT:

Claims 6-9, 11 and 12 are cancelled.

* * * * *